(12) United States Patent
Zalevsky et al.

(10) Patent No.: US 9,513,225 B2
(45) Date of Patent: Dec. 6, 2016

(54) METHOD AND SYSTEM FOR IMPROVING RESOLUTION OF A SPECTROMETER

(71) Applicant: BAR ILAN UNIVERSITY, Ramat Gan (IL)

(72) Inventors: Zeev Zalevsky, Rosh HaAyin (IL); Yair Hammer, Shoham (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 0 days.

(21) Appl. No.: 14/378,710

(22) PCT Filed: Feb. 11, 2013

(86) PCT No.: PCT/IL2013/050123
§ 371 (c)(1),
(2) Date: Aug. 14, 2014

(87) PCT Pub. No.: WO2013/121420
PCT Pub. Date: Aug. 22, 2013

(65) Prior Publication Data
US 2015/0233829 A1    Aug. 20, 2015

Related U.S. Application Data

(60) Provisional application No. 61/633,700, filed on Feb. 16, 2012.

(51) Int. Cl.
*G01J 3/44* (2006.01)
*G01N 21/65* (2006.01)
(52) U.S. Cl.
CPC ..... *G01N 21/65* (2013.01); *G01N 2201/06113* (2013.01); *G01N 2201/126* (2013.01)
(58) Field of Classification Search
CPC .......... G01J 3/26; G01J 3/44; G02B 26/001; G02B 26/0833
See application file for complete search history.

(56) References Cited

U.S. PATENT DOCUMENTS

| 5,194,912 A | 3/1993 | Batchelder et al. |
| 5,442,438 A * | 8/1995 | Batchelder ................ G01J 3/12 356/301 |

(Continued)

OTHER PUBLICATIONS

L. Andrew Lyon et al. Raman Spectroscopy "Anal. Chem." 70:341R-361R (1998).

(Continued)

*Primary Examiner* — Kara E Geisel
*Assistant Examiner* — Maurice Smith
(74) *Attorney, Agent, or Firm* — Browdy and Neimark, PLLC

(57) ABSTRACT

The present disclosure provides systems and methods for improving the resolution of a spectrometer configured to provide a frequency spectrum of a radiation incoming from a sample. The system comprises an optical medium configured so that the radiation incoming from the sample be transferred through the optical medium, the optical medium having a predetermined tunable spectral transmission curve; an operating unit connectable to the optical medium and configured to operate the optical medium so as to shift the spectral transmission curve of the optical medium over a predetermined spectral range; and a processing unit connectable to the spectrometer and configured to process a set of shifted frequency spectra provided by the spectrometer and obtainable by transferring the radiation incoming from the sample through the optical medium while shifting the spectral transmission curve of the optical medium so as to obtain a super resolved frequency spectrum of improved spectral resolution.

27 Claims, 7 Drawing Sheets

(56) References Cited

U.S. PATENT DOCUMENTS

| | | | |
|---|---|---|---|
| 7,327,453 B2 | 2/2008 | Coppeta | |
| 7,564,548 B2* | 7/2009 | Flanders | G01N 21/65 356/301 |
| 7,573,578 B2* | 8/2009 | Zribi | G02B 26/001 356/454 |
| 7,773,217 B2 | 8/2010 | Sriram et al. | |
| 8,830,465 B2* | 9/2014 | Taniguchi | G01N 21/9501 356/369 |
| 2001/0044129 A1* | 11/2001 | Ling | G01N 21/65 435/32 |
| 2005/0264808 A1 | 12/2005 | Wang | |
| 2009/0161943 A1* | 6/2009 | Yamashita | G01N 21/9501 382/149 |
| 2010/0241357 A1* | 9/2010 | Chan | G01J 3/44 702/19 |
| 2016/0161463 A1* | 6/2016 | Onuma | G01N 21/27 356/70 |

OTHER PUBLICATIONS

Dror Malka et al Super-Resolved Raman Spectroscopy. "Spectroscopy Letter" 46:307-313 (2013).

International search report. Application No. PCT/IL2013050123 dated Apr. 11, 2013.

* cited by examiner

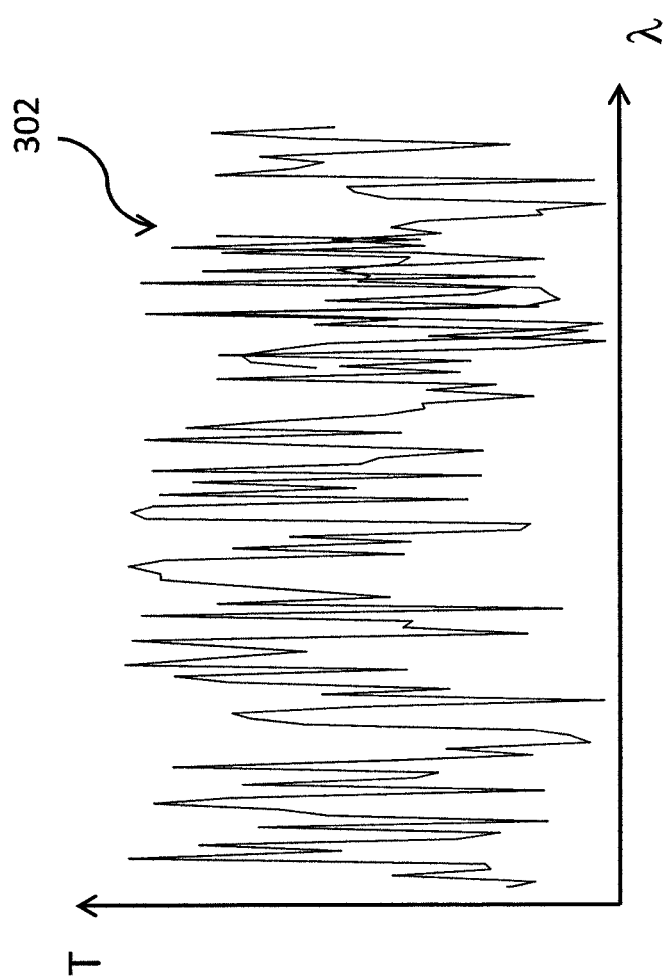

METHOD AND SYSTEM FOR IMPROVING RESOLUTION OF A SPECTROMETER

TECHNICAL FIELD

The present invention relates to the domain of spectrometry systems and methods. More particularly, the present invention relates to a system and method that can be used for improving the resolution of a spectrometry system, particularly in water quality monitoring applications.

BACKGROUND

Monitoring of chemicals in drinking water as well as in sewage water faces several major difficulties. First, a wide variety of chemicals should be monitored. For example, Nitride may be monitored since Nitride chemical competes with hemoglobin over oxygen and a high concentration of Nitride in water can cause so-called blue baby syndrome by preventing hemoglobin to arrive to blood. Techniques to monitor Nitride generally involve electrodes which become polluted thereby degrading quickly their efficiency. Ammonium may also be monitored since it is toxic to fish and other aquatic organisms. Phosphate may also be monitored since phosphate may cause development of alga and water weed which consume oxygen and destroy the water resources. Phosphate monitoring is especially important in agriculture and in sewage purification facilities. Techniques to monitor phosphate generally involve laboratory analysis and do not provide online real time analysis i.e. the results cannot be provided on site and have to be taken to a laboratory. Chloride may also be monitored since Chloride enable to determine the penetration of salty water in fresh water. Techniques to monitor Chloride generally also involve laboratory analysis. An alternative indirect measurement of Chloride may also be based on measuring conductivity although it is not precise and reliable. Boron may also be monitored in order to prevent damages to animals and plants. Particularly, real time Boron measurements in water desalination processes are of especially high importance since the removal of Boron during desalination processes is performed at high pH and pressure and is therefore costly. Thus, the ability to accurately measure the level of Boron may enable to avoid undue treatment.

In fact, techniques generally provide for continuous monitoring of only very few parameters like rate of flow, pressure, turbidity, pH, electrical conductivity and concentration of free Chlorine and do not provide with continuous monitoring of other chemical components concentrations. Even though some other techniques enable to detect a large plurality of chemical components, these alternative techniques adversely require laboratory analysis and do not provide with real time results. Further, most of the previously discussed techniques can only detect simultaneously a single chemical and generally require complicated maintenance operations which may include additions of chemical reagents, constant calibrations and high costs.

Spectrometry systems (also generally referred to as spectrometers) are used to measure properties of light over a specific portion of the electromagnetic spectrum. Spectrometry systems may advantageously be used to identify materials comprised in a sample according to the properties of light retrieved from the sample in so-called spectroscopic analysis. For example, Raman spectroscopy provides with a real time alternative to the aforementioned techniques. As described in L. A. Lyon, C. D. Keating, A. P. Fox, B. E. Baker, L. He, S. R. Nicewarner, S. P. Mulvaney and M. J. Natan, "*Raman Spectroscopy,*" *Anal. Chem.* 70, 341R-361R (1998) Raman-effect-based techniques are capable of providing identification of materials as well as estimating concentration of said materials in a sample. The Raman effect (also referred to as Raman scattering) is an optical non linear effect that is used in spectroscopy as a tool for mapping and detecting materials. The technique is based on illuminating the sample with a monochromatic incident radiation and on measuring a wavelength shift between the incident radiation and the reflected or transmitted radiation. The shift characterizes the material and allows its identification. The amount of absorption i.e. the value of the shifted peak may assist in estimation of the concentration of said material. The aforementioned technique produces valuable estimations and has been considered for designing sensors in chemical and biological contamination events. FIG. 1 illustrates the basic principle of Raman scattering in case of a Stokes shift. Raman scattering is an effect in which an illumination photon 1 of the incident radiation induces inelastic scattering in the non linear regime of a material 2. The scattering generates a Raman photon 3 with lower frequency (and energy) while the energetic difference (and therefore the frequency difference) is passed to the vibration states 4 of the material 2. Usually there are two shifts of wavelength in the reflected or transmitted radiation. In this inelastic interaction of the photons, the phonons are either created (Stokes shift) or annihilated (anti-Stokes). In one case the wavelength is increased (called anti-Stokes) and in the other it is decreased (called Stokes). Since the anti-Stokes radiations have generally a lower intensity than the Stokes radiations, only Stokes radiations may be considered in Raman spectrometry. The difference between the wavelengths of the Raman radiation and the incident radiation is only dependent on the properties of the material and not on the properties of the incident radiation. Therefore, it is possible to determine a Raman signature of the material. More particularly, the Raman signature of the material may be obtained as a Raman shift i.e. a difference between the Raman radiation wavelength and the incident radiation wavelength. Therefore, it is possible to detect the presence of the material in a sample by detecting a peak corresponding to the Raman radiation in the frequency spectrum of the reflected radiation. The position of the Raman radiation in the frequency spectrum may be detected around the wavelength of the incident radiation shifted of the Raman shift corresponding to the material. Further, knowing the wavelength of the incident radiation, the frequency spectrum to analyze may be reduced to a spectral band around the expected position.

A Raman spectroscopy configuration for detecting a predetermined material and estimating the concentration of said material in a sample has been therefore proposed in the prior art and involves a laser arranged at one side of a monitoring cell receiving the sample and a spectrometer at the other side of the monitoring cell. The spectrometer detects the presence of said material based on the presence of the Raman signature of the material in the frequency spectrum provided by the spectrometer. Indeed, the existence of the predetermined material in the monitoring cell generates an expected Raman shift. Further, the intensity of the Raman radiation i.e. the value of the shifted peak is proportional to the concentration of the material in the sample. Therefore, both types of information—presence and concentration—can be extracted.

General Description

However, spectrometry systems face difficulties in determining the presence of certain materials due to spectral resolution limitation of the spectrometer. For example, Raman spectrometry systems do not enable determining the presence in water of chemicals such as Boron, Arsenic, Perchlorate salts and heavy metals especially when said chemicals are present at low concentrations. Indeed, the spectral signatures of certain materials may be highly problematic to detect in a sample.

The present invention provides with a system and method which provides online and real time detection of a plurality of materials contained in a sample even when the spectral signatures of said materials are spectrally close and/or even when the concentration of said materials is very low. The sample may be a liquid, gas, solid, gel, slurry, powder, films, etc. In an embodiment, the sample may be water. In order to do so, the present invention proposes to super resolve the wavelength spectral information in a spectrometry configuration.

Resolution of an imaging system is defined as the capability to distinguish between two adjacent spatial features and consider them as two rather than a single larger one. The field of super resolution is the field in which the spatial information is encoded in such a way that another domains such as time, coherence, field of view, polarization or gray level are used in order to convert the spatial degrees of freedom that could not be resolved by the imaging system, and later on to decode them while constructing the spatially super resolved image. The process of conversion of spatial degrees of freedom into other domains is called multiplexing. For example, using the time domain to super resolve is called time multiplexing. In order to do this conversion of degrees of freedom one needs to know that the domains, into which the conversion takes place, have the availability to perceive the spatial information. For instance, if one uses time multiplexing and converts the spatial information into the temporal domain, he needs to know that the object being imaged is not varying in time during the time slot needed in order to increase the missing spatial resolution.

The added value in the spectral super resolving is related to obtaining an improved capability of detecting various chemicals (materials) as well as in the estimation of their concentration. This may be usefully applied to real time monitoring and evaluation of the quality of water. Therefore, a simplified, low cost multi functional monitoring system and method are presented. The present invention enables providing on-line and real time simultaneous estimation of several important materials in water as well as in other molecular samples such as gas, gels, solids, slurries, powders, films etc. The operation principle is based upon a new super resolved concept for spectrometry systems, particularly for Raman spectrometry. Although, as mentioned above, the temporal multiplexing is applied to super resolve the spectral distribution coming from a spectrometer. The operation principles may be understood in light of spatial information super resolving methods adapted to the spectrometry systems. By applying the proposed super resolving technique the obtainable spectral resolution can be significantly enhanced and leads to improved accuracy in the real time and in the on-line estimation capability of existing chemicals and their concentration in water as well as in other molecular samples such as gas, gels, solids, slurries, powders, films etc. The higher spectral resolution may also lead to the capability of monitoring several chemicals simultaneously with much higher accuracy in respect to the estimation of their concentration. For example, usage of super resolved spectral capability in Raman spectroscopy may provide detection capability with improved accuracy and precision of various chemicals in water e.g. Nitride, Ammonium, Phosphate, Chloride, Boron, Arsenic, Perchlorate salts, heavy metals, etc. Since the sharpness as well as the shape of the Raman peak is a finger print designating a specific material, the spectral resolution depends on its concentration. The height of the Raman peak is linked to the concentration of the chemical. The relation between spectral resolution and concentration is more or less linear. Therefore improvement of one order of magnitude in spectral resolution, as can be performed in the proposed super resolving approach, may yield one order of magnitude improvement in minimal detectable level of concentration and in its accuracy.

Following the description presented hereinafter it can be seen that a spectral resolution improvement can be obtained whenever there is a relative movement between the spectrum of the encoding medium and the spectrum that one wishes to super resolve. When using Raman spectroscopy a way to obtain relative spectral movement may be to use a fixed spectral encoding element and to tune the spectrum that we wish to map by changing the excitation wavelength of the Raman laser. However, in other types of spectroscopy one may realize the proposed concept as well by shifting the encoding spectrum function. This can be obtained in various ways for instance if the spectral encoding is realized via "handmade" devices such as predesigned spectral filters or various modified transmissions based upon Fabry-Perot resonators, then the spectral tuning can be obtained by applying electrical field, heating or mechanical movement over those filters in order to modify their spectral transmission (e.g. if one changes the distance between the mirrors of a Fabry-Perot resonator, its spectral transmission peaks will move). Other type of spectral encoding can be obtained by using "natural" means, e.g. to have a gas or a liquid or a solid having a defined transmission spectrum which fits our encoding purposes. In this case changing the pressure, volume or temperature of a gas (also for liquids and solids but in smaller amount) can modify its "natural" transmission curve.

An interesting point in the proposed technique is that most optical medium may be used as long as we know the spectral transmission curve of the medium in advance and in high resolution. Then the proposed processing can be performed enabling super-resolution. Still, the spectral transmission curve of the optical medium should contain high resolution spectral features (e.g. many sharp spectral peaks) in order to enable spectral encoding of the inspected spectral distribution.

Therefore, in a first aspect the presently disclosed subject matter provides a system for improving the resolution of a spectrometer, the spectrometer being configured to provide a frequency spectrum of a radiation incoming from a sample. The system comprises an optical medium configured so that the radiation incoming from the sample be transferred through the optical medium, the optical medium having a predetermined tunable spectral transmission curve; an operating unit connectable to the optical medium and configured to operate the optical medium so as to shift the spectral transmission curve of the optical medium over a predetermined spectral range; and a processing unit connectable to the spectrometer and configured to process a set of shifted frequency spectra provided by the spectrometer and obtainable by transferring the radiation incoming from the sample through the optical medium while shifting the spectral transmission curve of the optical medium so as to obtain a super resolved frequency spectrum of improved spectral resolution.

In a variant of the first aspect, the presently disclosed subject matter provides a system for improving the resolution of a spectrometer, the spectrometer being configured to provide a frequency spectrum of a radiation incoming from a sample illuminated with a tunable source of coherent radiation for generating a Raman emission in the sample. The system comprises: an optical medium configured so that the Raman emission generated by the sample is transferred through the optical medium, the optical medium having a predetermined spectral transmission curve; an operating unit connectable to the tunable source of coherent radiation and configured to shift a wavelength of the tunable source over a predetermined spectral range; a processing unit connectable to the spectrometer and configured to process a set of shifted frequency spectra provided by the spectrometer and obtainable by transferring the radiation incoming from the sample through the optical medium while shifting the wavelength of the tunable source so as to obtain a super resolved frequency spectrum of improved spectral resolution.

In some embodiments of the first and second variants, the optical medium is a tunable spectral filter.

In some embodiments of the first and second variants, the optical medium is a spectral filter sensitive to electrical field change.

In some embodiments of the first variant, the operating unit is configured to modify an electrical field of the optical medium so as to shift the spectral transmission curve of the optical medium over a predetermined spectral range.

In some embodiments of the first and second variants, the optical medium is a spectral filter sensitive to temperature, pressure and/or volume change.

In some embodiments of the first variant, the operating unit is configured to change a temperature, pressure and/or volume of the optical medium so as to shift the spectral transmission curve of the optical medium over a predetermined spectral range.

In some embodiments of the first and second variants, the optical medium is based on a Fabry-Perot resonator.

In some embodiments of the first variant, the operating unit is configured to modify a distance between two mirrors of the Fabry-Perot resonator so as to shift the spectral transmission curve of the optical medium over a predetermined spectral range.

In some embodiments of the first and second variants, the spectral transmission curve of the optical medium comprises spectral features of a spectral width smaller than a spectral resolution of the spectrometer.

In some embodiments of the first and second variants, the spectrometer is configured to detect a predetermined material in the sample and the spectral features are present in the spectral transmission curve of the optical medium in a spectral band comprising the wavelength of the predetermined material spectral signature.

In some embodiments of the first and second variants, the spectral band in which the spectral features are present has a spectral width substantially equal to the spectral resolution of the spectrometer.

In some embodiments of the second variant, the operating unit is configured to linearly shift the wavelength of the coherent source of radiation.

In some embodiments of the first variant, the operating unit is configured to linearly shift the spectral transmission curve of the optical medium.

In some embodiments of the first and second variants, the predetermined spectral range is at least as wide as a spectral resolution of the spectrometer.

In some embodiments of the first and second variants, the processing unit is configured to perform opposite time shifting, digital multiplication by the predetermined spectral transmission curve of the optical medium and time average on the set of shifted frequency spectra.

In some embodiments of the first and second variants, the optical medium is a gas phase.

In some embodiments of the first and second variants, the optical medium is a Bragg filter.

In some embodiments of the first and second variants, the processing unit is configured to detect in the sample any combination of chemicals, bacteria, medicine and drug.

In a second aspect, the presently disclosed subject matter provides a spectrometry system comprising a spectrometer configured to provide a frequency spectrum of a radiation incoming from a sample and a system according to any embodiment of the first or second variant of the first aspect previously described.

In some embodiments, the spectrometry system further comprises a tunable source of coherent light for generating a Raman emission in the sample.

In a third aspect the presently disclosed subject matter provides a water quality monitoring device comprising a monitoring cell or a basin configured to receive a water sample intended to be analyzed; and a system according to any embodiments of the first and second aspects previously described.

In a fourth aspect, the presently disclosed subject matter provides in a first variant a method of improving the resolution of a spectrometer configured to provide a frequency spectrum of a radiation incoming from a sample. The method comprises transferring the radiation incoming from the sample through an optical medium, the optical medium having a predetermined tunable spectral transmission curve; providing the radiation output by the optical medium to a spectrometer; shifting the spectral transmission curve of the optical medium over a predetermined spectral range; acquiring a set of shifted frequency spectra corresponding to a set of shift values of the shift of the spectral transmission curve; and processing the set of shifted frequency spectra so as to obtain a super resolved frequency spectrum of better resolution than the frequency spectrum.

In a second variant of the fourth aspect, the presently disclosed subject matter provides a method of improving the resolution of a spectrometer configured to provide a frequency spectrum of a radiation incoming from a sample. The method comprises illuminating a sample with a coherent radiation for generating a Raman emission in the sample; transmitting the Raman emission generated by the sample through an optical medium, the optical medium having a predetermined spectral transmission curve; providing the Raman emission output by the optical medium to a spectrometer; shifting a wavelength of the coherent radiation over a set of shifted wavelengths within a predetermined spectral range; acquiring a set of shifted frequency spectra corresponding to the Raman emissions transmitted through the optical medium for the set of shifted wavelengths; and processing the set of shifted frequency spectra so as to obtain a super resolved frequency spectrum of better resolution than the frequency spectrum.

In some embodiments of the first and second variants of the fourth aspect, the method further comprises determining if a predetermined material is contained in the sample based on the super resolved frequency spectrum.

In some embodiments of the first and second variants of the fourth aspect, the method further comprises determining a concentration of the material in the sample based on the super resolved frequency spectrum.

In some embodiments of the first and second variants of the fourth aspect, the spectral transmission curve of the optical medium comprises spectral features of a spectral width smaller than a spectral resolution of the spectrometer.

In some embodiments of the second variant of the fourth aspect, the spectral features are present around the wavelength of the Raman emission of the predetermined material to be detected.

In some embodiments of the second variant of the fourth aspect, shifting a wavelength of the coherent radiation comprises linearly shifting the wavelength of the radiation.

In some embodiments of the first and second variants of the fourth aspect, the predetermined spectral range is at least as wide as a spectral resolution of the frequency spectrum.

In some embodiments of the first and second variants of the fourth aspect, processing the set of shifted frequency spectra comprises opposite time shifting, digital multiplication by the predetermined spectral transmission curve of the optical medium and time average on the set of shifted frequency spectra.

In some embodiments of the first and second variants of the fourth aspect, the method further comprises detecting in the sample a concentration of any of nitride, ammonium, phosphate, chloride and boron based on the super resolved frequency spectrum.

In some embodiments of the first and second variants of the fourth aspect, the method further comprises detecting in the sample a concentration of any combination of chemicals, bacteria, hormone, medicine, drug, etc.

In some embodiments of the first and second variants of the fourth aspect, detecting in the sample comprises simultaneously detecting the concentration of any combination of chemicals, bacteria, hormone, medicine, drug, etc.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 8 illustrates a spectral transmission curve of an optical medium of a system according to an embodiment of the second variant of the present invention.

DETAILED DESCRIPTION OF EMBODIMENTS

As explained above, the present invention is based on a spectrometry system and in certain aspects aims at determining presence and concentration of chemicals (materials) in a water sample. The present invention notably enables to obtain the following advantageous properties: versatility, non destructive measurement, accuracy and modularity. Indeed, the same basic principle can be applied for a large variety of materials. Further, the measurement of the sample does not cause any transformation, heating, dilution, etc. to the sample. Furthermore, the present invention provides with a high end measuring approach allowing high and controllable sensitivity for concentration estimation. Eventually, the present invention can be integrated with other optics related concepts allowing expanding the overall range of performance for the proposed concentration identification system.

Figure 1:
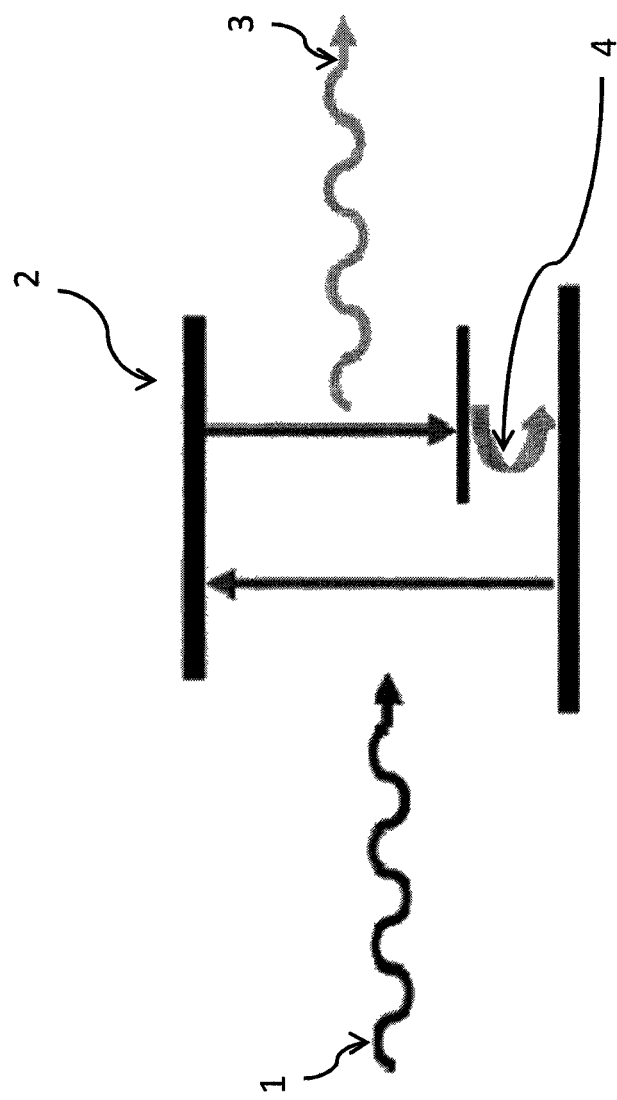
FIG. 1, previously described, illustrates the basic principle of the Raman effect.
Figure 2A:
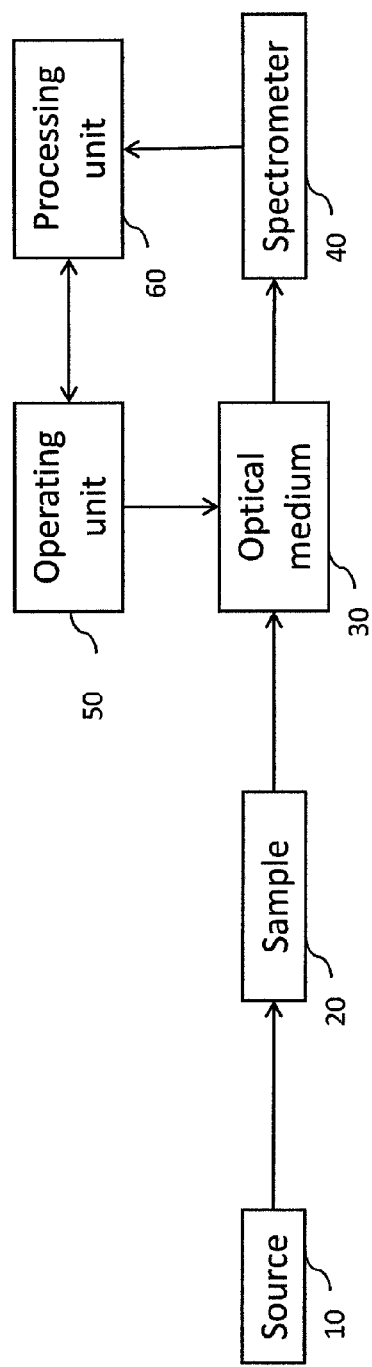
FIG. 2A is a block diagram schematically illustrating elements of a spectrometry system for spectrally analyzing a sample according to a first variant of the present invention.

FIG. 2A is a block diagram illustrating generally a spectrometry system for analyzing a sample 20 according to a first variant of the present invention. The spectrometry system includes an optical medium 30 having a tunable spectral transmission curve, a spectrometer 40, an operating unit 50 and a processing unit 60. The system may also include a source 10.

The sample 20 may provide an electromagnetic radiation to be analyzed by the spectrometer 40. The electromagnetic radiation may be any of Raman radiation, infrared (IR) radiation, ultra-violet (UV) radiation, gamma-ray radiation, X radiation, etc. The radiation incoming from the sample 20 may be generated by the source 10 or may result from natural emission of the sample 20. The sample 20 may contain one or more predetermined material to be detected in the sample 20 by analyzing a frequency spectrum provided by the spectrometer 40 on a given spectral band. The predetermined material may have a characteristic spectral signature in said spectral band. In the following, the frequency spectrum of the radiation incoming directly from the sample 20 (without traversing the optical medium 30) is referred to as the original frequency spectrum and may be provided by the spectrometer 40 when the optical medium 30 is not present in the system.

Figure 2B:
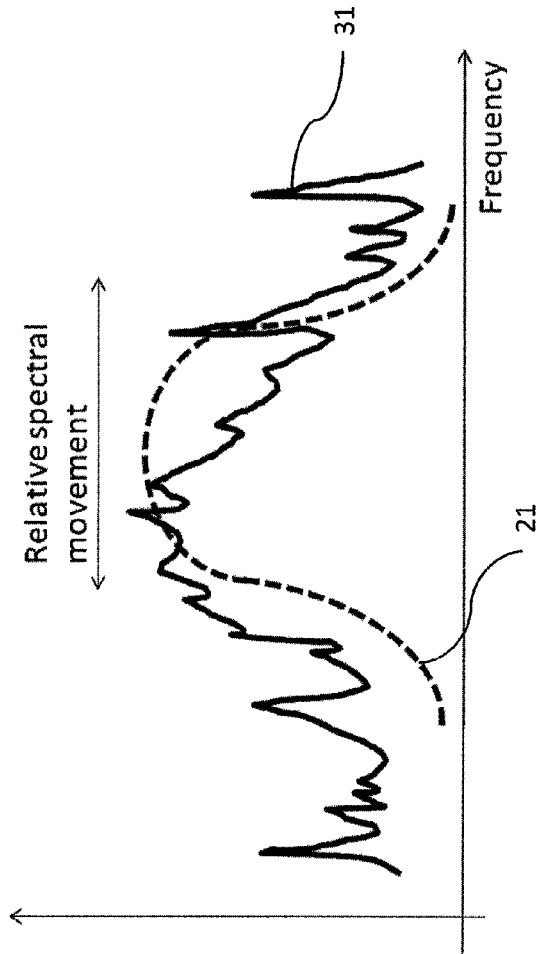
FIG. 2B illustrates a relative spectral movement between a spectral transmission curve of an optical medium and a frequency spectrum of a material in a method according to the present invention.

The optical medium 30 may be configured so that a radiation incoming from the sample traverses the optical medium 30 before being analyzed by the spectrometer 40 i.e. the optical medium 30 is positioned downstream of the sample 20 and upstream of the spectrometer 40 with regard to the direction of propagation of the radiation to be analyzed. FIG. 2B presents a spectral transmission curve 31 of the optical medium 30 and the original frequency spectrum 21 for a given operating state of the optical medium 30. The spectral transmission curve 31 of the optical medium 30 may contain fine spectral features. The optical medium may act as a spectral encoding medium. The spectral transmission curve 31 of the optical medium 30 may be defined by the feature that a Fourier transform of the transmission curve 31 may be a wideband function. The width $\Delta\lambda$ of the finest spectral elements in the spectral transmission curve 31 of the optical medium 30 may correspond to the final spectral resolution achieved by the super resolution process described in more details hereinafter. The fine spectral features may be present in the spectral transmission curve of the optical medium in a spectral band comprising the wavelength of the predetermined material spectral signature. The optical medium 30 may be a tunable spectral filter whose spectral transmission curve may be modified according to an operating state of the optical medium 30 among a set of operating states of the optical medium 30. The optical medium 30 may for example be sensitive to electrical field change, to temperature, pressure and/or volume change and the set of operating states of the optical medium 30 may for example refer to different values of at least one of the aforementioned parameters. In an embodiment, the optical medium 30 may be configured so that the spectral transmission curve corresponding to the set of operating states is obtained by a translation of the spectral transmission curve in an initial operating state. The spectral transmission curve of the optical medium 30 corresponding to said set of operating states may be obtained by translating (shifting) the spectral transmission curve towards higher and/or lower frequencies. For example the optical medium may be a gas phase. The optical medium may alternatively be a Fabry Perot resonator and be operated by modification of the resonator frequency by modifying a distance between two mirrors of the resonator. The optical medium may alternatively be a Bragg filter.

The spectrometer 40 may be configured to receive the radiation output by the optical medium 30 and provide a frequency spectrum of said radiation. The spectrometer 40 may comprise a separator, collimation elements and a detector (not shown). The spectral resolution of the spectrometer may be set by the arrangement of the aforementioned elements.

The operating unit 50 may enable to modify the operating state of the optical medium 30 over time. In the embodiment in which the spectral transmission curve of the optical medium can be translated according to the operating state of the optical medium 30, the operating unit 50 may be configured to operate the optical medium 30 so as to shift the transmission curve of the optical medium 30 over a predetermined spectral bandwidth i.e. to translate the transmission curve of the optical medium 30 towards lower and/or higher frequencies. In some embodiments, the shift of the spectral transmission curve caused by operating the operating unit 50 may be linear over time on a predetermined spectral bandwidth.

From a general standpoint and as described hereinafter with regard to an embodiment of the invention, the frequency spectrum obtained by providing the radiation output by the optical medium 30 to the spectrometer 40 results from the multiplication of the spectral transmission curve 31 of the optical medium by the original frequency spectrum 21 of the sample 20. Further, by operating the optical medium 30 though the operating unit 50 so as to create a relative spectral movement between the original frequency spectrum 21 and the spectral transmission curve 31, it is possible to acquire a set of shifted frequency spectra. As described hereinafter with regard to an embodiment of the invention, the processing of the set of shifted frequency spectra respectively acquired for a set of operating states of the optical medium 30 enables to obtain a super resolved frequency spectrum. The processing may require to preliminary know the transmission curve of the optical medium 30 for the different operating states at which the set of shifted frequency spectra are acquired. In an embodiment, this may be achieved by knowing the spectral transmission curve of the optical medium 30 in an initial operating state and the relative movement created by the operation of the optical medium 30 through the operating unit 50.

The processing unit 60 may be connectable to the spectrometer 40. Further, the processing unit 60 may be configured to process the set of shifted frequency spectra provided by the spectrometer 40 and resulting from the radiations transmitted through the optical medium 30 for the set of operating states of the optical medium 30. The processing unit 60 may be configured to receive data indicative of the set of operating states corresponding to the set of shifted frequency spectra. The shifted frequency spectra are acquired by the spectrometer 40 and processed by the processing unit 60. As described in more details with reference to FIG. 4-5, processing of the set of shifted frequency spectra may enable to obtain a super resolved frequency spectrum of improved spectral resolution.

Figure 3A:
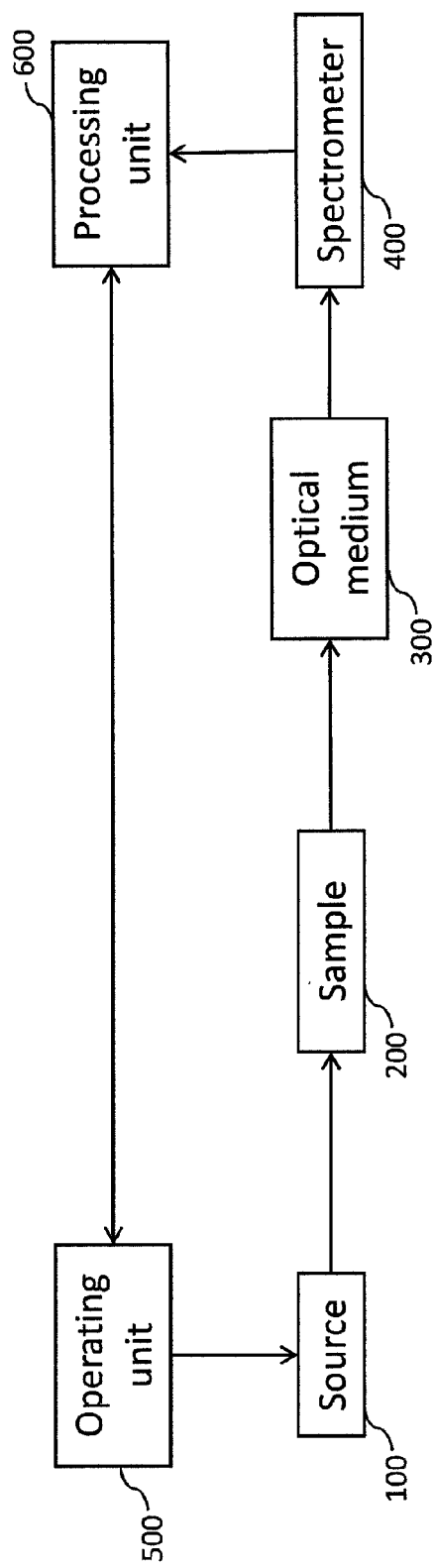
FIG. 3A is a block diagram schematically illustrating elements of a system for improving spectral resolution of a Raman spectrometer according to a second variant of the present invention and FIG. 3B illustrates spectral properties of the elements shown on FIG. 3A.

FIG. 3A is a block diagram illustrating generally a Raman spectrometry system for analyzing a sample 200 according to a second variant of the invention. The system includes a tunable source of coherent radiation 100, an optical medium 300, a spectrometer 400, an operating unit 500 and a processing unit 600.

The second variant of the present invention implements an idea equivalent to the first variant but the relative movement between the spectral transmission curve of the optical medium and the frequency spectrum is obtained by operating a tunable source instead of operating a tunable optical medium. In fact, when using Raman spectroscopy a direct way to obtain relative spectral movement between the spectral transmission curve of the optical medium and the frequency spectrum of the radiation incoming from the sample may be given by using a fixed spectral encoding element and by tuning the wavelength of the source generating a Raman radiation in the sample. Indeed, an interesting property of the Raman effect that fits to the proposed approach is that when one tunes the wavelength of the excitation source, the Raman emission generated from the inspected sample is also shifted accordingly.

Figure 3B:
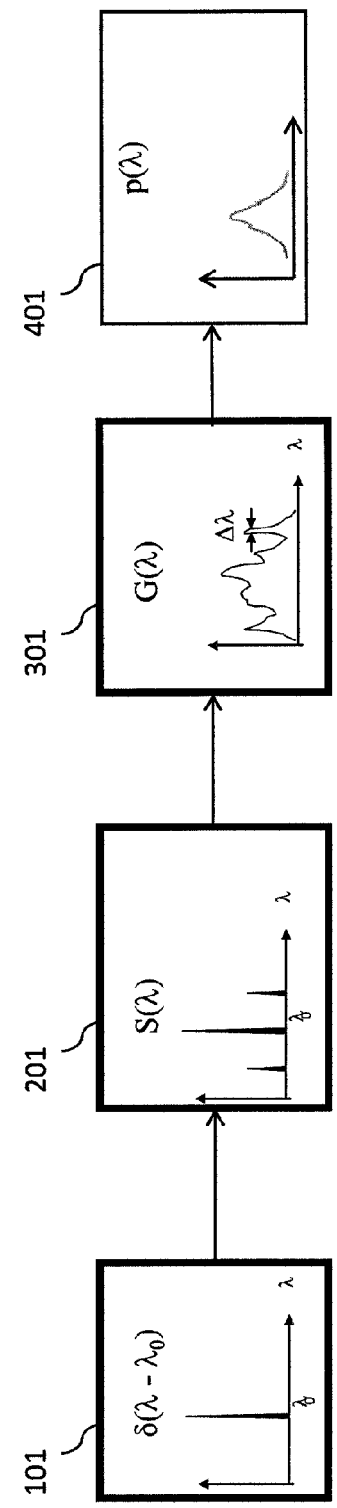

The tunable source of coherent radiation 100 may be configured to illuminate the sample 200 for generating a Raman emission in the sample 200. The tunable source of coherent radiation may be tunable over a predetermined spectral range of a few nanometers or more generally on a spectral range at least as wide or substantially as wide as the spectral resolution of the spectrometer 400. The tunable source of coherent radiation 100 may for example be a Diode Pumped Solid State laser (DPSS). The system may further comprise a monitoring cell for receiving the sample 200. The source 100 may be configured to illuminate one illumination wall of the monitoring cell. FIG. 3B presents a spectral profile 101 of the radiation emitted by the source of coherent radiation 100. As can be seen on FIG. 3B the radiation emitted is substantially monochromatic. FIG. 3B further presents the spectral profile 201 of the radiation output by the sample 200 in the case of Raman emission in the sample 200 and the spectral profile 401 of the resolution $p(\lambda)$ of the spectrometer 400.

The optical medium 300 may be configured so that the Raman emission generated by the sample 200 is transmitted through the optical medium 300. The optical medium may have a priori known spectral transmission curve. FIG. 3B presents a spectral transmission curve 301 of the optical medium 300 in an embodiment of the invention. Particularly, the spectral transmission curve 301 of the optical medium 30 may contain fine spectral features. The width $\Delta\lambda$ of the finest spectral elements in the spectral transmission curve 301 of the optical medium 300 may correspond to the final spectral resolution achieved by the super resolution process described in more details hereinafter with reference to FIGS. 4-5. For example, the optical medium 300 may comprise a gas phase, a Fabry-Perot filter or a Bragg filter. FIG. 8 also illustrates a spectral transmission curve 302 of the optical medium in an embodiment of the invention. As can be seen, the spectral transmission curve 302 contains small spectral features. In other words, the optical medium acts as a spectral encoding medium and the spectral transmission curve 301, 302 of the optical medium 300 may be defined by the feature that a Fourier transform of the transmission curve 301, 302 may be a wideband function.

The spectrometer 400 may be configured to receive the Raman emission transmitted through the optical medium 300 and provide a frequency spectrum of said Raman emission. In the embodiment in which the system comprises a monitoring cell, the spectrometer 400 may be arranged at a wall opposite to the illumination wall on which radiation from the source of coherent radiation 100 impinges. The resolution of the spectrometer 400 may be linked to a point spread function of the spectrometer 400 expressed as:

$$p(\lambda) = \exp\left(\frac{-\lambda}{2\sigma_\lambda^2}\right), \quad (1)$$

wherein $\sigma_\lambda$ is related to the spectral resolution of the spectrometer i.e. the spectral width of the spectral scanning point spread function. FIG. 3B presents a point spread function 401 of the spectrometer 400 in an embodiment of the invention. The spectral read out (also referred to as frequency spectrum) captured by the spectrometer 400 may be expressed by:

$$\int S(\lambda')G(\lambda')p(\lambda-\lambda')d\lambda' \quad (2)$$

wherein $S(\lambda)$ is the spectral emission coming from the sample due to the Raman effect (also referred to as the spectral distribution of the Raman emission) and $G(\lambda)$ the spectral transmission of the optical medium 300. It is understood that corresponding equations may apply as well in the first variant of the invention.

The operating unit 500 may be connectable to the tunable source of coherent radiation 100. The operating unit 500 may be operable to tune a wavelength of the tunable source of coherent radiation 100. Particularly, the operating unit 500 may be configured to shift a wavelength of the tunable source of coherent radiation 200 over a set of shifted wavelengths within the predetermined spectral band over which the source is tunable. In an embodiment, the operating unit 500 may be configured to shift the wavelength of the coherent source of radiation 100 over time on the predetermined spectral bandwidth. Particularly, the predetermined spectral band may be of a width substantially equal to the spectral resolution of the spectrometer $3\sigma_\lambda$. The spectrometer 400 may acquire a set of shifted frequency spectra resulting from the Raman emission transmitted through the optical medium 300 at said set of shifted wavelengths within the predetermined spectral band. The operating unit 500 may further be configured to send to the processing unit 600 data indicative of the predetermined spectral band.

The processing unit 600 may be connectable to the spectrometer 400. Further, the processing unit 600 may be configured to process the set of shifted frequency spectra provided by the spectrometer 400 and resulting from the Raman emissions transmitted through the optical medium 300 for the set of shifted wavelengths. The processing unit 600 may be configured to receive data indicative of the set of shifted wavelengths corresponding to the set of shifted frequency spectra. The shifted frequency spectra are further processed by the processing unit 600. As described in more details with reference to FIG. 4-5, processing of the set of shifted frequency spectra may enable to obtain a super resolved frequency spectrum of improved spectral resolution.

Figure 4:
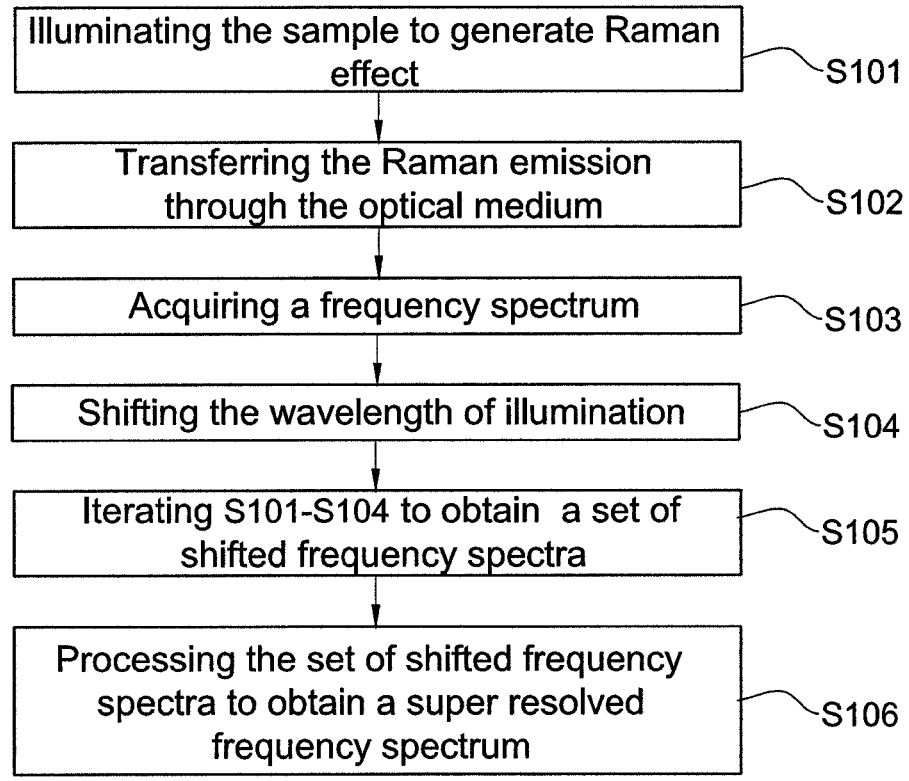
FIG. 4 is a flow diagram illustrating generally a method for improving the spectral resolution of a spectrometer according to an embodiment of the second variant of the present invention.

FIG. 4 is a flow diagram illustrating general steps of a method for improving the resolution of a Raman spectrometry system according to the second variant of the present invention. In a first step S101, the sample is illuminated by a coherent source of radiation so as to generate a Raman effect in the sample. In a second step S102, a Raman emission generated by the sample is passed through an optical medium. The spectral transmission curve of the optical medium is fixed and known and contains small spectral features as explained hereinabove. In a third step S103, the radiation output from the optical medium is provided to a spectrometer thereby providing a frequency spectrum. In a fourth step S104, the wavelength of the coherent source is shifted and a shifted frequency spectrum is obtained. In an embodiment, the shift of the source is a linear shift over time on a predetermined spectral range. In a fifth step S105, steps S101-S104 are iterated so that the wavelength of the coherent source is shifted over a set of shifted wavelengths and a set of shifted frequency spectra is acquired. In a sixth step S106, the set of shifted frequency spectra is processed so as to obtain a super resolved frequency spectrum.

A very interesting property of the Raman effect that fits to the proposed approach is that when one tunes the wavelength of the strong excitation laser, the Raman emission generated from the inspected medium is also shifted accordingly. Considering that the spectral shift of the source of coherent radiation is linearly changed in time and equals to $\delta\lambda=\delta vt$ where t is the time axis and $\delta v$ is the spectral scanning velocity, the shifted frequency spectrum for a wavelength of the coherent source equal to $\lambda'-\delta\lambda$ becomes:

$$S''(\lambda) = \int S(\lambda'-\delta vt)G(\lambda')p(\lambda-\lambda')d\lambda' \quad (3)$$

By changing the variables, the previous relation can be expressed as:

$$S''(\lambda) = \int S(\lambda'')G(\lambda''+\delta vt)p(\lambda-\lambda''-\delta vt)d\lambda'' \quad (4)$$

It is understood that corresponding equations may apply as well in the first variant described hereinabove in the case of a linear shift of the spectral transmission curve of the optical medium relatively to the frequency spectrum.

Figure 5:
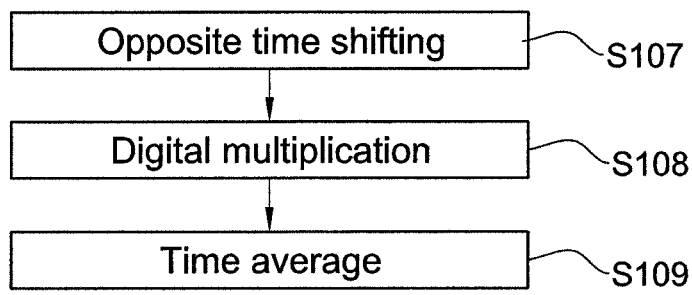
FIG. 5 is a flow diagram illustrating further steps of a processing for obtaining a super resolved frequency spectrum from a set of shifted frequency spectra according to the present invention.

FIG. 5 is a flow diagram illustrating the processing of the set of shifted frequency spectra when the tunable source is linearly shifted over time. It is to be noted that a corresponding reasoning may be obtained for a linear shift of the optical medium spectral transmission curve relatively to the frequency spectrum according to the first variant of the invention. In a first step S107, opposite time shifting may be performed i.e. $S''(\lambda+\delta vt)$ is obtained. In a second step S108, digital multiplication of the data by the fixed and a priori known encoding spectrum $G(\lambda)$ is performed i.e. $S''(\lambda+\delta vt)G(\lambda+\delta vt)$ is obtained. In a third step S109, time average is performed i.e. summing of all the readouts processed according to steps S107-S108 i.e. $\int S''(\lambda+\delta vt)G(\lambda+\delta vt)dt$ is obtained. The obtained results lead to a super resolved frequency spectrum $S_R(\lambda)$ i.e. a reconstructed high resolution spectrum of the analyzed sample.

The following calculations illustrate the result of the processing of steps S107-S109:

$$S_R(\lambda) = \int S''(\lambda + \delta vt)G(\lambda + \delta vt)dt \quad (5)$$

$$= \int \left[ \int S(\lambda'')G(\lambda'' + \delta vt)p(\lambda - \lambda'')d\lambda'' \right] G(\lambda + \delta vt)dt$$

By changing the order of integration, it is possible to obtain:

$$S_R(\lambda) = \int [\int G(\lambda''+\delta vt)G(\lambda+\delta vt)dt]S(\lambda'')p(\lambda-\lambda'')d\lambda'' \quad (6)$$

Due to orthogonality property of the optical medium one has $$\int G(\lambda''+\delta vt)G(\lambda+\delta vt)dt = \delta(\lambda''-\lambda)+\kappa \quad (7)$$

where $\kappa$ is a constant and $\delta$ is the Delta function of Dirac. This orthogonality property arises from the fact that the spectral transmission of the optical medium is very non uniform, non periodic and varying with $\lambda$. Thus, small shift of this transmission in $\lambda$ is no longer correlated with the non shifted transmission. Following that, the obtained result is:

$$S_R(\lambda) = \int \delta(\lambda'' - \lambda)S(\lambda'')p(\lambda - \lambda'')d\lambda'' + \quad (8)$$

$$\kappa \int S(\lambda'')p(\lambda - \lambda'')d\lambda''$$

$$= p(0)S(\lambda) + \kappa S(\lambda) \otimes p(\lambda)$$

where $\otimes$ designated the mathematical operation of convolution.

Assuming that $p(0)$ is not zero, in the first term we have the full reconstruction of the Raman spectral emission of the inspected medium without dependence on the original spectral mapping resolution of the spectrometer (which corresponds to the spectral width of $p(\lambda)$). The second term is the original spectral mapping obtained by the spectrometer at its original resolution without the super resolved effect.

It is to be noted that the delta function of Equation (7) is as narrow as $\Delta\lambda$ in the spectral transmission curve of the optical medium and this is why the finest spectral detail in the fixed spectral transmission medium determines the final resolution to be obtained in the super resolved reconstruction process. If instead of Eq. 7 we assume a more realistic expression of:

$$\int G(\lambda'' + \delta vt)G(\lambda + \delta vt)dt = \exp\left(-\frac{(\lambda - \lambda'')^2}{2(\delta\lambda)^2}\right) + \kappa \quad (9)$$

then the reconstructed distribution of Eq. 8 becomes:

$$S_R(\lambda) = \int \exp\left(-\frac{(\lambda - \lambda'')^2}{2(\delta\lambda)^2}\right)S(\lambda'')p(\lambda - \lambda'')d\lambda'' + \quad (10)$$

$$\kappa \int S(\lambda'')p(\lambda - \lambda'')d\lambda''$$

$$= \left[p(\lambda)\exp\left(-\frac{\lambda^2}{2(\delta\lambda)^2}\right)\right] \otimes S(\lambda) + \kappa S(\lambda) \otimes p(\lambda)$$

$$\approx \left[p(0)\exp\left(-\frac{\lambda^2}{2(\delta\lambda)^2}\right)\right] \otimes S(\lambda) + \kappa S(\lambda) \otimes p(\lambda)$$

since $p(\lambda)$ is much wider than the Gaussian of Eq. 9 the approximation of Eq. 10 is valid.

The result presented by Equation (10) shows that the super resolution of the spectrometer using the proposed processing corresponds to $\Delta\lambda$ rather than being proportional to $\sigma_\lambda$ which is the spectral width of $p(\lambda)$ (the original resolution of the spectrometer). The improvement factor can be an order of magnitude which significantly affects the accuracy and the concentration precision of the chemicals that are to be estimated using the system of the invention.

Further, the processing of the set of shifted frequency spectra may also comprise subtraction of the low resolution second term $\kappa S(\lambda) \otimes p(\lambda)$ of Equation (8) so as to use only the super resolved term.

It is to be noted that similar results can be obtained for a non linear shifting in time of the wavelength of the tunable laser. In this case, equation (7) becomes:

$$\int G(\lambda''+g(t))G(\lambda+g(t))dt = \delta(\lambda''-\lambda)+\kappa$$

where $g(t)$ is the temporal function representing the change in the wavelength. In fact, a requirement for performing the above described method is to know the temporal function $g(t)$ i.e. to shift the wavelength of the tunable source of coherent radiation over a predetermined set of shifted wavelengths. Further, it is understood that a similar reasoning is also possible in the case of the first embodiment of the invention in which the optical medium spectral transmission curve is shifted relatively to the frequency spectrum.

Figure 6:
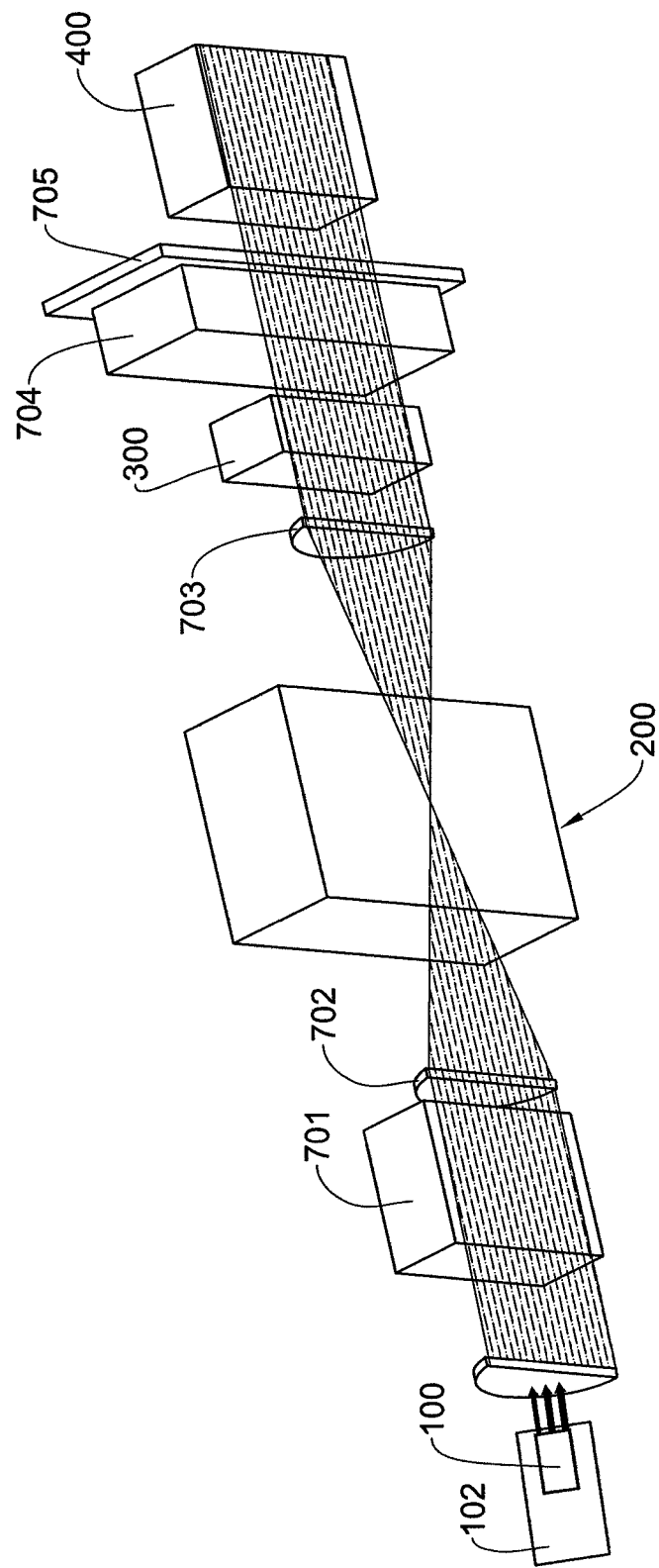
FIG. 6 illustrates a spectrometry system according to an embodiment of the second variant of the present invention.

FIG. 6 illustrates a system to spectrally analyze a sample according to an embodiment of the invention. Same numeral references between FIG. 3 and FIG. 6 refer to the same elements and only additional elements of FIG. 6 are hereunder described. The system now described includes a tunable source of coherent radiation 100, an optical medium 300, a spectrometer 400, an operating unit (not shown) and a processing unit (not shown). Further, the system comprises a mount 102, a polarized beam splitter 701, a focusing lens 702, a collecting lens 703, a liquid crystal cell 704 and a polarizer 705. In the following description, the term upstream and downstream refer to the light propagation direction from the source of coherent light 100 to the spectrometer 400.

Note that the proposed system can further be folded by using optical fibers to transmit radiation to and from the sample 200 instead of regular free space propagation. This may enable to reduce the dimensions of system so as to obtain a reduce the volume of the system.

The mount 102 may be configured to hold the source of coherent radiation 100. The polarized beam splitter 701 may be arranged downstream of the source of coherent radiation 100 and upstream of the sample 200. The focusing lens 702 may be arranged downstream of the polarized beam splitter and upstream of the sample 200 and configured to focus a radiation beam from the source of coherent radiation 100 on the sample 200. The collecting lens 703 may be arranged downstream of the sample 200 and configured to collect a radiation beam output by the sample 200 on the spectrometer 400. The liquid crystal cell 704 may be arranged downstream of the optical medium 300 and upstream of the spectrometer 400. The liquid crystal cell 704 may be configured to modify a polarization state of an incoming radiation. The polarizer may be arranged downstream of the liquid crystal cell 704 and upstream of the spectrometer 400. The combination of the polarized beam splitter 701, the liquid crystal cell 704 and the polarizer 705 enables to obtain additional capabilities by using the polarization property of the source of coherent radiation to perform several measurements simultaneously since the two orthogonal polarization states may not interfere with each other even if having the same wavelength. Thus, using the two orthogonal states of polarization may allow simultaneous analyzing of two different chemicals.

Figure 7:
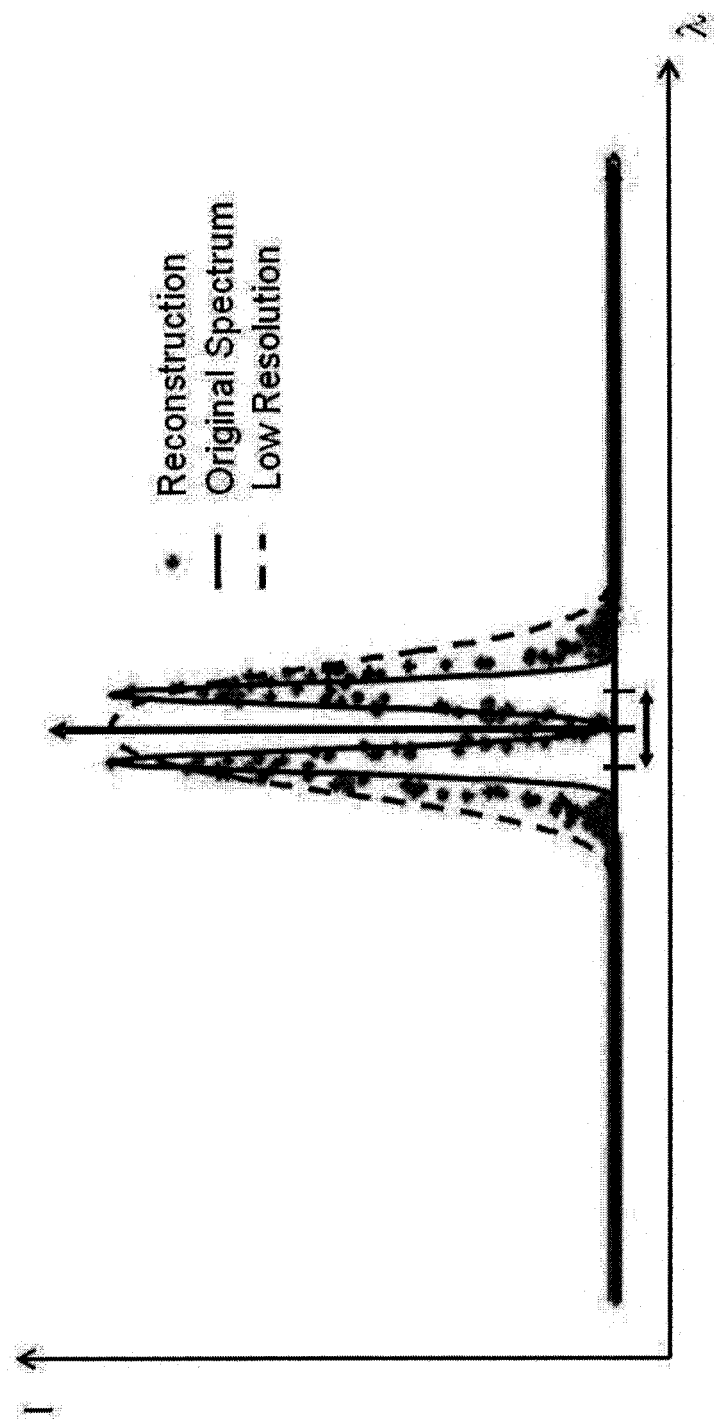
FIG. 7 illustrates a numerical simulation of a super resolved frequency spectrum obtained by a system according to an embodiment of the second variant of the present invention.

FIG. 7 illustrates a simulated example of the proposed method according to an embodiment of the second variant of the invention. The Raman signature of two different chemicals is represented by a solid line. Said Raman signature comprises two spectral peaks spectrally close. The frequency spectrum obtained by a Raman spectrometer according to the prior art analyzing the sample containing the two chemicals is represented by a dashed line. The two peaks cannot be resolved by such spectrometer. However, by acquiring a plurality of shifted frequency spectra through an optical medium by shifting the wavelength of a tunable source according to the present disclosure, it is possible to obtain a super resolved frequency spectrum as previously described. The super resolved frequency spectrum is represented by reconstruction dots on FIG. 7. It is possible to notice that after applying the proposed method with the fixed spectral transmission generator (also referred to as optical medium in the description) the two peaks can now be resolved and the two chemicals can now be identified.

Therefore, the present invention presents a novel system and method for enhancing spectral resolution of spectrometry systems. The method and system may be used for the design of a real-time water quality monitoring device. The improved spectral resolution of the system according to the invention may assist in better separation between several chemicals available in the water simultaneously and in better estimation of their concentration.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A system for improving the resolution of a spectrometer in a spectrometry system, the system comprising:
    an optical medium having a predetermined tunable spectral transmission curve the optical medium being configured for accommodating downstream of a sample and upstream of a spectrometer, such that radiation from the sample, propagating towards the spectrometer, passes though the optical medium, said predetermined tunable spectral transmission curve of the optical medium comprising spectral features of a spectral width smaller than a spectral resolution of the spectrometer;
    an operating unit having one of the following configurations:
    (a) the operating unit is associated with the optical medium and is configured to apply to the optical medium at least one effect inducing a change in an operating state of the optical medium shifting the spectral transmission curve of the optical medium over a predetermined spectral range
    (b) the operating unit is configured to connect to a tunable source of coherent radiation to irradiate the sample, and to affect a change in at least one operating parameter of the tunable source to shift an operating wavelength of the tunable source over a predetermined spectral range; and
    a processing unit configured to connect to the spectrometer and configured and operable to receive spectrometry data from the spectrometer, the spectrometry data comprising a set of shifted frequency spectra from the sample corresponding to the shift provided by the operating unit, the processing unit configured and operable to process the spectrometry data to obtain a super resolved frequency spectrum of improved spectral resolution.

2. The system of claim 1, comprising the tunable source, said tunable source is configured and operable to generate a Raman emission in the sample, the operating unit being configured to connect to the tunable source to shift the wavelength of the tunable source over the predetermined spectral range.

3. The system according to claim 1, wherein the optical medium is a tunable spectral filter.

4. The system according to claim 1, wherein the operating unit is configured and operable to apply to said optical medium at least one of the following effects: electrical field, temperature, pressure fields, a volume change, thereby causing the change in the operating state of the optical medium shifting the spectral transmission curve thereof over a predetermined spectral range.

5. The system according to claim 1, wherein the optical medium is based on a Fabry-Perot resonator.

6. The system according to claim 5, wherein the operating unit is configured to connect to the optical medium and is configured and operable to affect a distance between two mirrors of the Fabry-Perot resonator causing a volume change of the optical medium and thus causing said change in the operating state of the optical medium so as to shift the spectral transmission curve of the optical medium over a predetermined spectral range.

7. The system according to claim 1, wherein the spectrometer is configured and operable to detect a predetermined material in the sample and the spectral features are present in the spectral transmission curve of the optical medium in a spectral band comprising the wavelength of the predetermined material spectral signature.

8. The system according to claim 7, wherein the spectral band in which the spectral features are present has a spectral width substantially equal to the spectral resolution of the spectrometer.

9. The system according to claim 1, wherein the operating unit is configured and operable to linearly shift either the wavelength of the coherent source of radiation or the spectral transmission curve of the optical medium.

10. The system according to claim 1, wherein the predetermined spectral range of the tunable source is at least as wide as a spectral resolution of the spectrometer.

11. The system according to claim 1, wherein the processing unit is configured and operable to utilize data indicative of the spectral shift induced by the operating unit to perform time shifting of the set of shifted frequency spectra, digital multiplication by the predetermined spectral transmission curve of the optical medium and time average on the set of shifted frequency spectra.

12. The system according to claim 1, wherein the optical medium is a gas phase.

13. The system according to claim 1, wherein the optical medium is a Bragg filter.

14. The system according to claim 1, wherein the processing unit is configured and operable to detect in the sample any combination of chemicals, bacteria, medicine and drug.

15. A spectrometry system comprising a spectrometer configured and operable to provide a frequency spectrum of a radiation incoming from a sample and a system according to claim 1, the frequency spectrum provided by the spectrometer being indicative of the set of shifted frequency spectra.

16. The spectrometry system according to claim 15 further comprising a tunable source of coherent light to generate a Raman emission in the sample, the operating unit being configured to connect to the tunable source to shift the wavelength of the tunable source over the predetermined spectral range.

17. A water quality monitoring device comprising:
- a monitoring cell or a basin configured and operable to receive a water sample intended to be analyzed; and
- a spectrometry system according to claim 15.

18. A method for use in a spectrometry system for improving the resolution of a spectrometer, the method comprising:
- transferring radiation incoming from a sample through an optical medium having a predetermined tunable spectral transmission curve comprising spectral features of a spectral width smaller than a spectral resolution of the spectrometer, and providing radiation output of the optical medium to a spectrometer;
- affecting either a coherent illumination of the sample or the optical medium, so as to provide either shifting of a wavelength of the coherent radiation over a set of shifted wavelengths within a predetermined spectral range, or shifting the spectral transmission curve of the optical medium over a predetermined spectral range;
- acquiring a set of shifted frequency spectra from the sample corresponding to a set of shift values of the shift of either the wavelength of the coherent radiation or the spectral transmission curve; and
- processing the set of shifted frequency spectra so as to obtain a super resolved frequency spectrum of better resolution than the frequency spectrum.

19. The method of claim 18, wherein said illuminating radiation comprises coherent radiation for generating a Raman emission in the sample.

20. The method according to claim 19, wherein the spectral features are present around the wavelength of the Raman emission of a predetermined material in the sample to be detected.

21. The method according to claim 18, further comprising determining if a predetermined material is contained in the sample based on the super resolved frequency spectrum.

22. The method according to claim 18, further comprising determining a concentration of a predetermined material in the sample based on the super resolved frequency spectrum.

23. The method according to claim 18, wherein shifting a wavelength of the coherent radiation comprises linearly shifting the wavelength of the radiation.

24. The method according to claim 18, wherein the predetermined spectral range is at least as wide as a spectral resolution of the frequency spectrum.

25. The method according to claim 18, wherein processing the set of shifted frequency spectra comprises time shifting, digital multiplication by the predetermined spectral transmission curve of the optical medium and time average on the set of shifted frequency spectra.

26. The method according to claim 18, further comprising detecting in the sample a concentration of any of nitride, ammonium, phosphate, chloride and boron based on the super resolved frequency spectrum.

27. The method according to claim 18, further comprising detecting in the sample a concentration of any combination of chemicals, bacteria, hormone, medicine, drug.

* * * * *